(12) United States Patent
Nakata et al.

(10) Patent No.: US 7,769,130 B2
(45) Date of Patent: Aug. 3, 2010

(54) X-RAY IMAGING APPARATUS

(75) Inventors: Hajime Nakata, Kanagawa (JP); Katsumi Hirabayashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/236,528

(22) Filed: Sep. 24, 2008

(65) Prior Publication Data

US 2009/0086928 A1 Apr. 2, 2009

(30) Foreign Application Priority Data

Sep. 28, 2007 (JP) .............................. 2007-256453

(51) Int. Cl.
*A61B 6/04* (2006.01)
*H05G 1/02* (2006.01)
(52) U.S. Cl. .......................... 378/37; 378/195; 378/208
(58) Field of Classification Search .................. 378/37, 378/195, 208
See application file for complete search history.

(56) References Cited

U.S. PATENT DOCUMENTS

| | | | | |
|---|---|---|---|---|
| 3,824,397 | A * | 7/1974 | Bauer et al. .................... | 378/37 |
| 4,979,196 | A * | 12/1990 | Lieutaud et al. ................ | 378/37 |
| 5,594,769 | A * | 1/1997 | Pellegrino et al. .............. | 378/37 |
| 5,820,552 | A * | 10/1998 | Crosby et al. ................. | 600/407 |
| 6,882,700 | B2 * | 4/2005 | Wang et al. .................... | 378/37 |
| 6,966,695 | B2 * | 11/2005 | Boomgaarden et al. ..... | 378/177 |
| 7,041,109 | B2 * | 5/2006 | Dowlatshahi ................ | 606/130 |
| 7,133,490 | B2 * | 11/2006 | Muller et al. .................. | 378/37 |
| 7,327,825 | B2 * | 2/2008 | Roncaglioni et al. .......... | 378/37 |
| 7,469,031 | B2 * | 12/2008 | Hyvarinen et al. ............ | 378/37 |
| 7,639,778 | B2 * | 12/2009 | Kashiwagi .................... | 378/37 |

FOREIGN PATENT DOCUMENTS

JP 2006-150077 A 6/2006

* cited by examiner

*Primary Examiner*—Edward J Glick
*Assistant Examiner*—Thomas R Artman
(74) *Attorney, Agent, or Firm*—Sughrue Mion, PLLC

(57) ABSTRACT

An X-ray imaging apparatus is disposed with an imaging table that includes an imaging surface with which a breast of an examinee in an upright posture is brought into contact and handles that are disposed higher than the imaging surface during craniocaudal imaging. Grip portions of the handles slant so as to gradually become closer to a chest wall contacting portion as the grip portions approach the imaging surface. Thus, when an examinee is made to grasp the handles, the posture of the examinee can be made more natural.

11 Claims, 9 Drawing Sheets

X-RAY IMAGING APPARATUS

CROSS-REFERENCE TO RELATED APPLICATION

This application claims priority under 35 USC 119 from Japanese Patent Application No. 2007-256453, the disclosure of which is incorporated by reference herein.

BACKGROUND OF THE INVENTION

1. Field of the Invention

The present invention relates to an X-ray imaging apparatus for medical use.

2. Description of the Related Art

In the current medical equipment industry, the emergence of competition is fierce and various devices are being developed due to various social backgrounds. In accompaniment with this increase and maturity of competition in the medical equipment industry, the development of apparatus that are more comfortable for patients than has conventionally been the case is being sought after.

One example of such an apparatus is an X-ray imaging apparatus (mammography machine) that images the breasts of an examinee for the purpose of early detection of breast cancer and the like.

However, it has been common for this conventional X-ray imaging apparatus to image the breasts of the examinee while the examinee is in an unnatural posture where the examinee is made to keep the arms straight without bending the elbows.

As a countermeasure to this, in Japanese Patent Application Publication (JP-A) No. 2006-150077, there is proposed forming recessed shapes or projecting shapes that can be used as handles or armrests on the sides of the portion of the apparatus that supports the breasts.

However, it is preferable to the examinee for X-ray imaging apparatus to be able to image the breasts of the examinee while the examinee is in a more natural posture.

SUMMARY OF THE INVENTION

In view of these circumstances, it is an object of the present invention to provide an X-ray imaging apparatus that can make an examinee comfortable and image the examinee by making the posture of the examinee more natural.

A first aspect of the present invention is an X-ray imaging apparatus that images the breasts of an examinee, the examinee's upper body having an upright posture, the X-ray imaging apparatus comprising: an imaging table that includes an imaging surface with which at least one breast of the examinee is brought into contact; and apparatus grasping portions that are disposed higher than the imaging surface during craniocaudal imaging, the grasping portions being configured to be graspable by the hands of the examinee, and slant so as to gradually become closer to the examinee as the grasping portions approach the imaging surface.

In this manner, in the X-ray imaging apparatus of the first aspect of the present invention, the grasping portions are disposed higher than the imaging surface during craniocaudal imaging and slant so as to gradually become closer to the examinee as the grasping portions approach the imaging surface. Consequently, when the examinee is made to grasp the grasping portions, the posture of the examinee can be made more natural. Thus, the examinee can be made comfortable and imaged.

In the X-ray imaging apparatus of the first aspect of the present invention, handles that include bar-like grip portions that are equal to or greater than a predetermined length may be disposed as the grasping portions.

The predetermined length is a length that is not too short in consideration of the height of the examinee and the arm length of the examinee.

According to this configuration, the examinee can reliably and easily grip the handles that serve as the grasping portions.

In the X-ray imaging apparatus of the first aspect of the present invention, the grip portions may slant in accordance with the average height of the examinee.

According to this configuration, it is easy to maintain the comfort of the examinee even when the height of the examinee varies.

In the X-ray imaging apparatus of the first aspect of the present invention, the grip portions may slant in accordance with the average arm length of the examinee.

According to this configuration, it is easy to maintain the comfort of the examinee even when the arm length of the examinee varies.

In the X-ray imaging apparatus of the first aspect of the present invention, the grip portions may slant by an angle within the range of $20°\pm10°$ in a front direction of the examinee during craniocaudal imaging with respect to a normal line direction of the imaging surface.

When the grip portions slant within the above-described range, they are comfortable for the examinee.

In the X-ray imaging apparatus of the first aspect of the present invention, a distance from a point of intersection between an extension plane of the imaging surface and an oblique centerline of the grip portions to an edge portion of the imaging surface on the examinee side may be within the range of 350 mm±50 mm.

When the above-described distance is longer than 400 mm, a patient who is short gradually ends up spreading apart the elbows, and it is easy for the feeling of comfort of the examinee to be impaired. Further, when the above-described distance is shorter than 300 mm, the feeling of comfort on the part of the patient is not impaired that much, but it is easy for negative effects to arise, such as it becoming difficult for a technician doing positioning to remove his/her hands after holding down the breast of the patient because of the arms of the patient.

In the X-ray imaging apparatus of the first aspect of the present invention, a height position of upper ends of the grip portions during craniocaudal imaging may be equal to or greater than 200 mm from the imaging surface.

When the above-described height position of the upper ends of the grip portions is less than 200 mm, it is easy for the function of positioning during craniocaudal imaging and the function of the grip portions serving as armrests during mediolateral oblique imaging with respect to a patient who is tall to be impaired.

In the X-ray imaging apparatus of the first aspect of the present invention, the handles may be formed integrally with the imaging surface.

In this configuration, the comfort of the armrests can be promoted because joints disappear. Further, when the imaging table is rotated in order to perform mediolateral oblique imaging, the handles rotate together with the imaging table and function as armrests.

In the X-ray imaging apparatus of the first aspect of the present invention, the handles may be configured by soft members.

Thus, the feeling of gripping the handles is comfortable for the examinee.

According to the present invention, there can be provided an X-ray imaging apparatus that can make an examinee comfortable and image the examinee by making the posture of the examinee more natural.

DETAILED DESCRIPTION OF THE INVENTION

Figure 1:
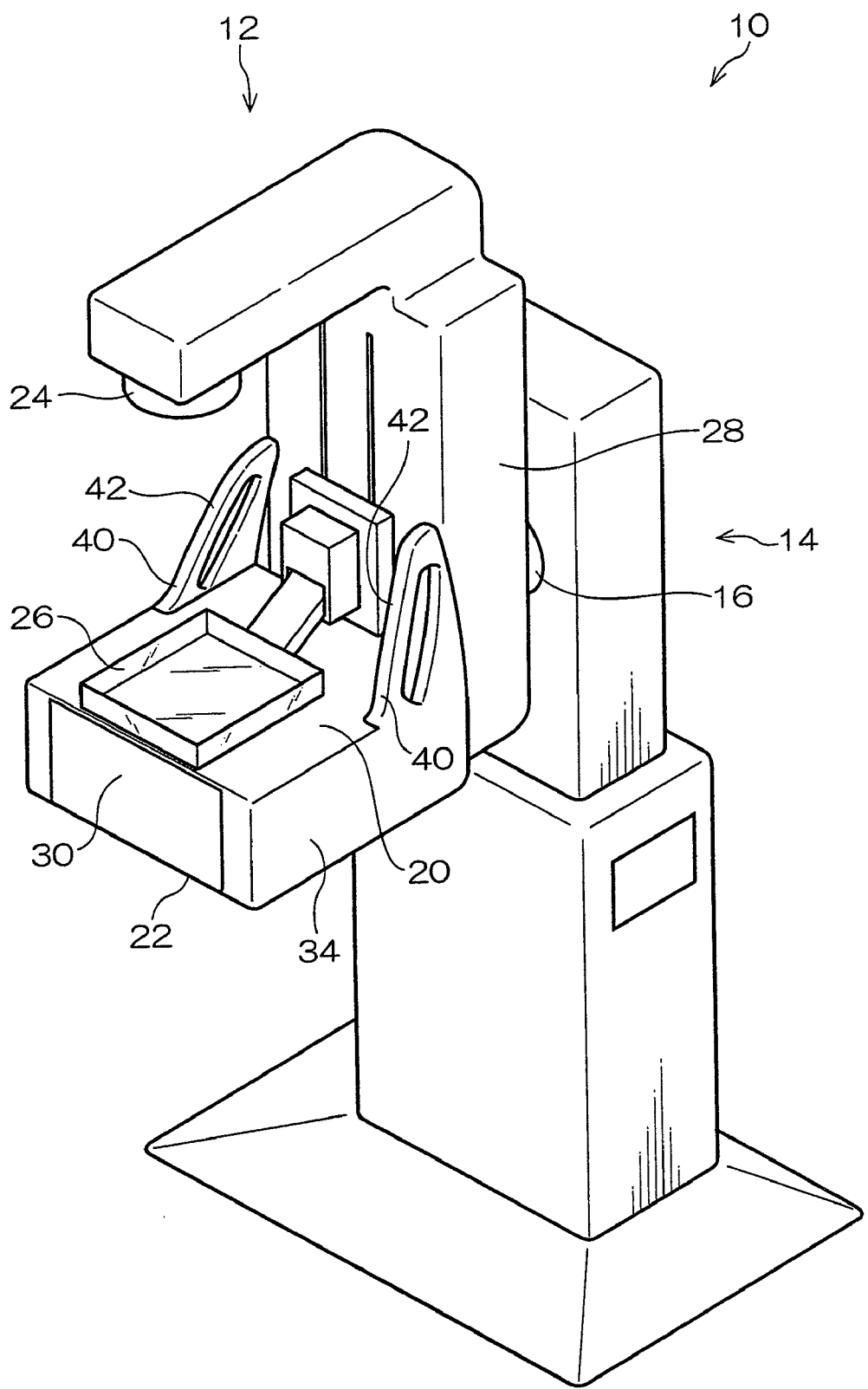
FIG. 1 is a perspective view of an X-ray imaging apparatus pertaining to an embodiment of the present invention.

Below, a mode of implementing the present invention will be described by way of an embodiment. FIG. 1 is a perspective view of an X-ray imaging apparatus (mammography machine) 10 pertaining to the embodiment of the present invention. The X-ray imaging apparatus 10 is an apparatus that images at least one breast of an examinee in an upright posture with X rays and can perform both CC (craniocaudal) imaging and MLO (mediolateral oblique) imaging.

The X-ray imaging apparatus 10 is disposed with a measuring portion 12 that is disposed on the front side of the apparatus and is substantially C-shaped when seen from the side and a base portion 14 that supports the measuring portion 12 from the rear. A rotating shaft 16 that extends rearward and is rotatably supported on the base portion 14 is disposed in the measuring portion 12. The rotating shaft 16 is supported on the base portion 14, whereby the measuring portion 12 is rotatably supported on the base portion 14.

The measuring portion 12 is disposed with an imaging table 22 on which is formed a planar imaging surface 20 that contacts a breast N (see FIG. 3) of an examinee (patient) W in an upright posture, a radiation irradiation portion 24 in which an X-ray tube (not shown) is disposed and which irradiates the imaging surface 20 with X rays for detection, a pressing plate 26 that presses the breast N of the examinee W against the imaging surface 20, and a holding portion 28 that holds the imaging table 22, the radiation irradiation portion 24 and the pressing plate 26. The holding portion 28 holds the imaging table 22 and the radiation irradiation portion 24 such that the imaging surface 20 and the radiation irradiation portion 24 are separated by a predetermined distance and slidably holds the pressing plate 26 such that the distance between the pressing plate 26 and the imaging surface 20 is variable.

The imaging table 22 includes a chest wall contacting portion 30 that is formed on the front side of the imaging table 22 and with which the portion of the chest that is lower than the breast N of the examinee W (see FIG. 3) is brought into contact during CC imaging. The front side of the chest wall contacting portion 30 is planar.

Inside the imaging table 22, there is disposed a radiation detector (not shown) that is irradiated with radiation passing through the imaging surface 20.

Figure 2:
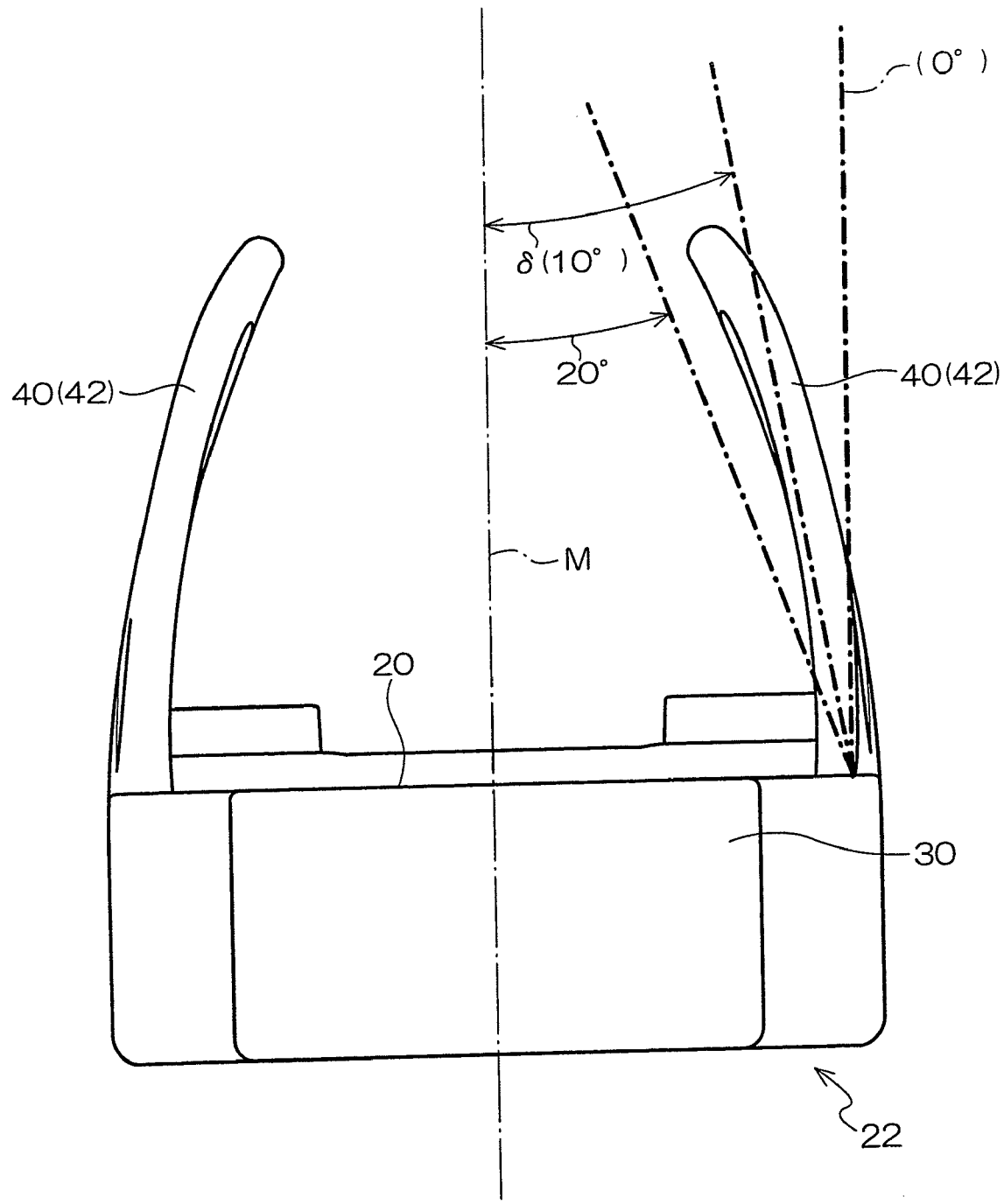
FIG. 2 is a schematic front view of an imaging table that configures the X-ray imaging apparatus pertaining to the embodiment of the present invention.
Figure 3:
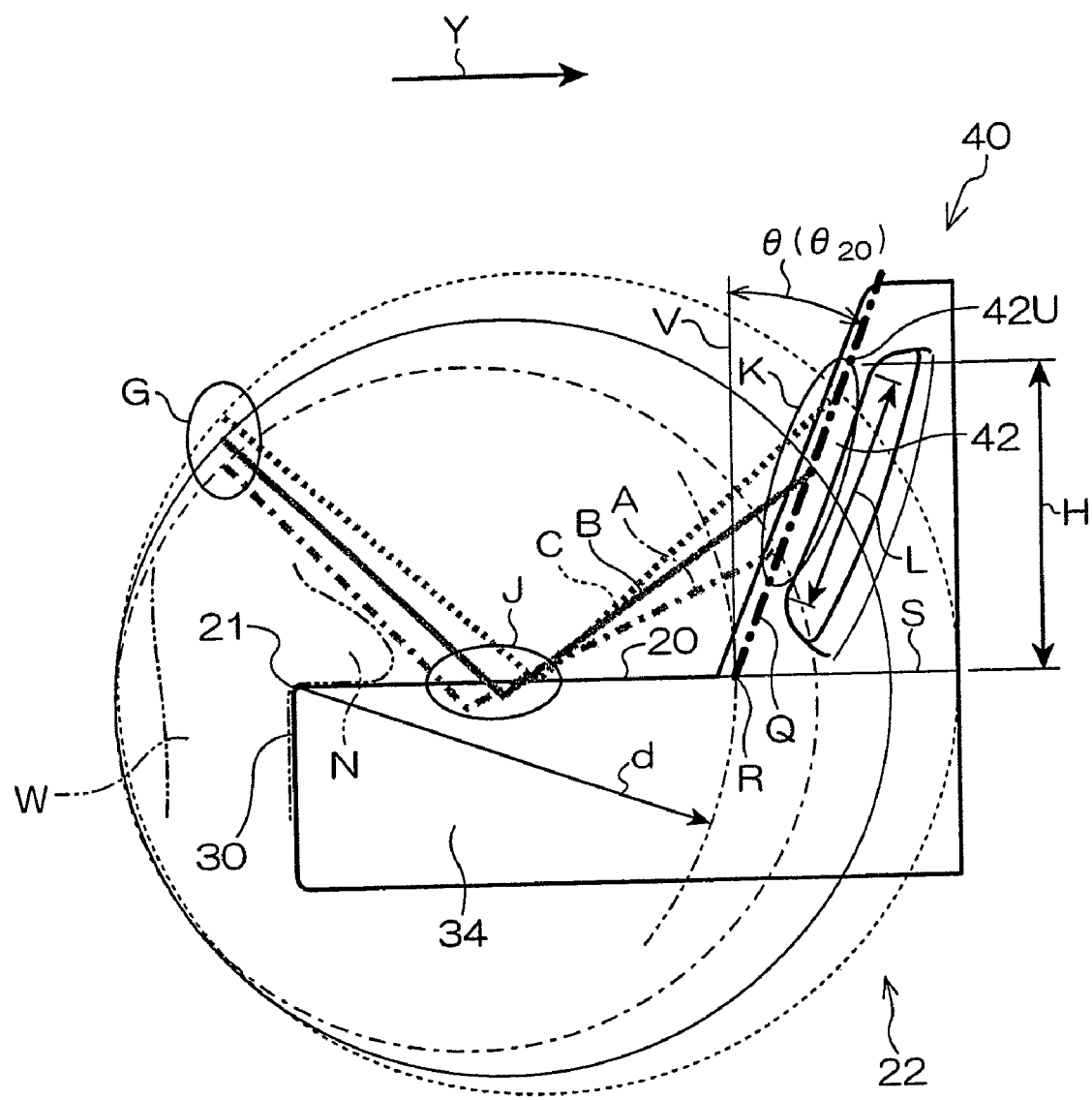
FIG. 3 is a schematic side view describing an examinee being able to grip handles in a natural posture, regardless of whether the examinee is tall or short or whether the arms of the examinee are long or short, during CC imaging in the X-ray imaging apparatus pertaining to the embodiment of the present invention.

Moreover, as shown in FIG. 1 to FIG. 3, a pair of handles 40 that the examinee W grasps with both hands during CC imaging is integrally formed on the imaging table 22 on the radiation irradiation portion 24 side of the imaging surface 20. Grip portions 42 that configure the handles 40 and are gripped by the examinee W are configured as substantially straight bars that slant toward the opposite side of the examinee W side (that is, the deep side with respect to the examinee W) with respect to a normal line of the imaging surface 20 and gradually become closer to the examinee W as the grip portions 42 approach the imaging surface 20; that is, the grip portions 42 gradually become closer to the chest wall contacting portion 30. Consequently, during CC imaging, the disposed height of the pair of handles 40 is higher than the imaging surface 20, and the pair of handles 40 slant from their upper portions to their lower portions so as to gradually become closer to the examinee W. It will be noted that the handles 40 are configured by soft members.

A length L (see FIG. 3) of the grip portions 42 is set to be equal to or greater than a predetermined length. The predetermined length is a length where each examinee W can grasp the grip portions 42 in a natural posture in consideration of the height and arm length of the examinee W. In the present embodiment, L is set to be equal to or greater than 200 mm. Further, a height position H of upper ends 42U of the grip portions 42 from the imaging table 22 during CC imaging is set to be equal to or greater than 200 mm.

Further, the grip portions 42 slant in accordance with the average height and average arm length of the examinee W. In the present embodiment, the grip portions 42 slant by an angle-of-inclination θ (below, this will be called a front side angle-of-inclination θ) within the range of 20°±10° in a front direction Y (see FIG. 3) of the examinee W during CC imaging—that is, toward the deep side of the apparatus—with respect to a normal line direction V of the imaging surface 20 (see FIG. 3, FIG. 5 and FIG. 6). It will be noted that this angle range corresponds to the range of 70°±10° with respect to the imaging surface 20.

Further, a distance d from an edge portion 21 of the imaging surface 20 on the examinee W side to a point of intersection R between an extension plane S of the imaging surface 20 and an oblique centerline Q of the grip portions 42 is set within the range of 350 mm±50 mm.

Further, as shown in FIG. 2, the pair of handles 40 gradually curve toward the inside of the imaging surface 20—that is, toward a plane M (below, this will be called an imaging center plane M) that is orthogonal to the imaging surface 20 and includes an imaging surface centerline that extends toward the front side (the examinee W side)—as the handles 40 recede from the imaging surface 20. Further, the handles 40 curve somewhat so as to become concave on the inside of the imaging surface 20. In the present embodiment, an angle-of-inclination angle δ of the handles 40 with respect to the imaging center plane M (that is, an angle-of-inclination δ of the grip portions 42 with respect to the imaging center plane M; below, this will be called an inside angle-of-inclination δ) is set within the range of 0° to 20°.

(Action and Effects)

Below, the action and effects of the present embodiment will be described using the attached drawings. In the following description, a state of the arms that is uncomfortable for the examinee (patient) W will be defined as a state where the arms of the examinee W are folded or a state where the arms of the examinee W are extended stiffly. Conversely, a state of the arms that is comfortable for the examinee W will be defined as a state of arms that is not uncomfortable for the examinee W and where the examinee W does not put unreasonable force in the arms.

In FIG. 3, arm positions that are comfortable for the examinee W when the arms of the examinee (patient) W are positioned during CC imaging are indicated by broken line A (a faint and fat one-dotted chain line), broken line B (a faint and fat solid line) and broken line C (a faint and fat dotted line). The line types indicated by broken lines A to C represent differences in the height of the examinee W: the faint and fat one-dotted chain line (the line type of broken line A) supposes a height of about 150 cm, the faint and fat solid line (the line type of broken line B) supposes a height of about 165 cm, and the faint and fat dotted line (the line type of broken line C) supposes a height of about 180 cm. The heights of the examinee W that the three faint line types represent will be common in the present specification. It will be noted that, during CC imaging, the elbows of the examinee W are brought into contact with side wall surfaces 34 (see FIG. 1 and FIG. 2) of the imaging table 22. Further, in FIG. 3, the aforementioned distance d is shown as being 350 mm.

During CC imaging, the position of the shoulders of the examinee W and the position of the elbows of the examinee W resulting from differences in the height of the examinee W differ depending on the height of the examinee W. In FIG. 3, region G represents a range in which the shoulders are positioned, region J represents a range in which the elbows are positioned, and region K represents a region in which the hands are positioned.

Here, in FIG. 3, the circle indicated by the narrow one-dotted chain line is a circle drawn using the elbow of an examinee represented by the faint and fat one-dotted chain line (broken line A) as the center and using the length of the hand of the examinee as the radius. The circle indicated by the narrow solid line is a circle drawn using the elbow of an examinee represented by the faint and fat solid line (broken line B) as the center and using the length of the hand of the examinee as the radius. The circle indicated by the narrow dotted line is a circle drawn using the elbow of an examinee represented by the faint and fat dotted line (broken line C) as the center and using the length of the hand of the examinee as the radius. It will be understood by these circles that the handle gripping position that is comfortable for the examinee W whose chest portion has been brought into contact with the chest wall contacting portion 30 is on the deeper side of the imaging table 22 (that is, the far side from the chest wall contacting portion 30) the taller the examinee W is.

Consequently, by setting the front side angle-of-inclination θ of the grip portions 42 to $\theta_{20}$=20°, that is, by disposing the grip portions 42 along the straight oblique centerline Q represented by the dark and fat one-dotted chain line in FIG. 3, examinees of whatever height can position their arms comfortably.

Figure 4:
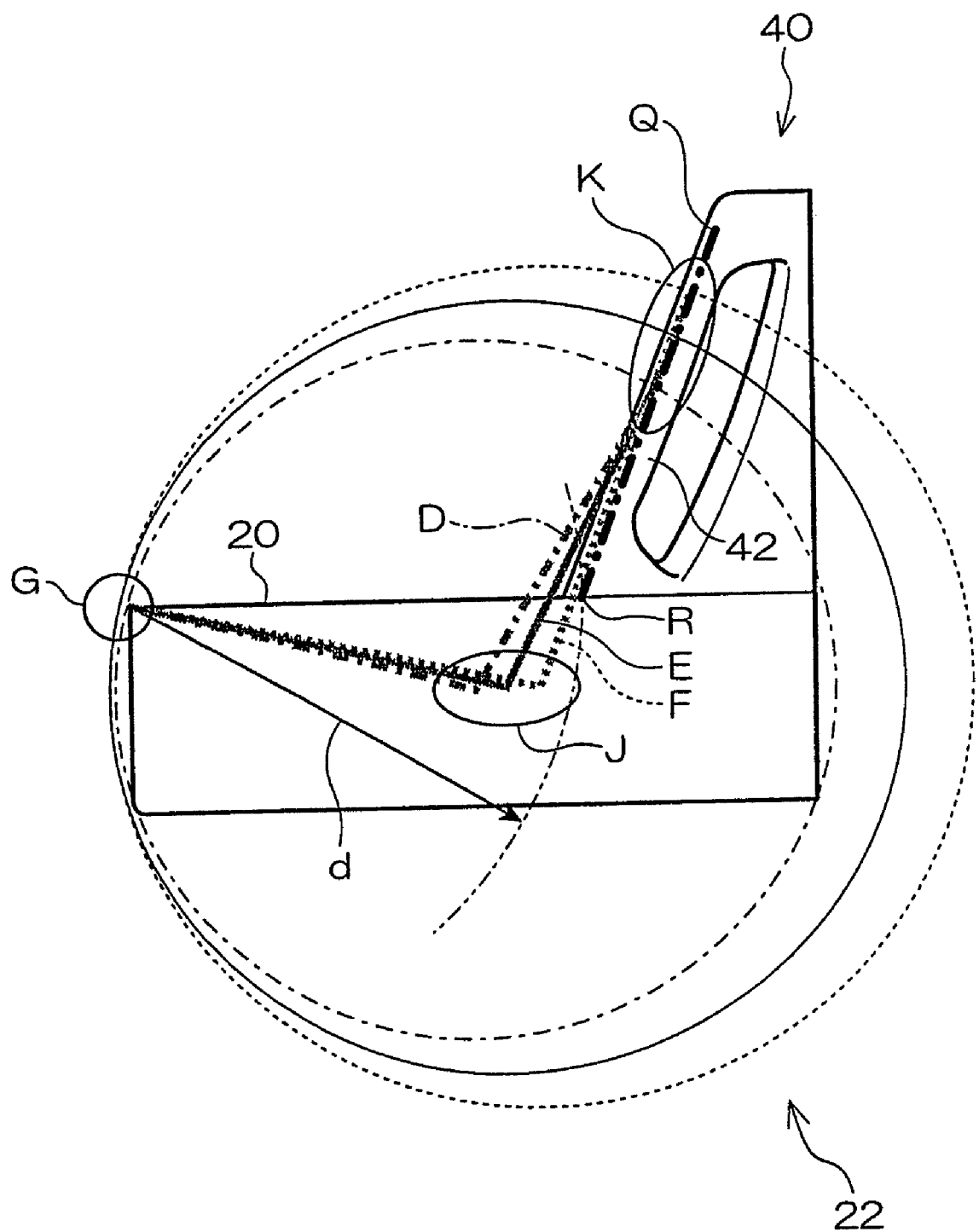
FIG. 4 is a schematic plan view describing an examinee being able to use the handles as armrests in a natural posture, regardless of whether the examinee is tall or short or whether the arms of the examinee are long or short, during MLO imaging in the X-ray imaging apparatus pertaining to the embodiment of the present invention.

In FIG. 4, arm positions that are comfortable for the examinee W when the arms of the examinee W are positioned during MLO imaging are indicated by broken lines A to C.

During MLO imaging, usually the imaging table 22 is rotated 60° to 90° in comparison to during CC imaging, and the examinee W is positioned such that the armpits of the examinee W are brought into contact with the corner portion of the side wall of the imaging table 22. Here, the position of the shoulders of the examinee W generally coincides with the edge portion 21 of the imaging surface 20 on the examinee W side, and the position of the elbows of the examinee W resulting from differences in height is gradually toward the deep side of the imaging table 22 (that is, the far side from the chest wall contacting portion 30) depending on the height of the examinee W.

It will be understood that, at this time, straight line D (the faint and fat one-dotted chain line), straight line E (the faint and fat solid line) and straight line F (the faint and fat dotted line), which represent positions from the elbow to the hand of the examinee W, are all positioned on the grip portions 42 whose front side angle-of-inclination θ that was appropriate during CC imaging is $\theta_{20}$ (20°). That is, in positioning during MLO imaging, the grip portions 42 are positioned along the straight oblique centerline Q represented by the dark and fat one-dotted chain line in FIG. 4, whereby the effect is recognized that the grip portions 42 function as armrests that are comfortable for examinees of whatever height.

Below, a range of disposed positions of the grip portions 42 that is preferable for the examinee W will be described.

Figure 5:
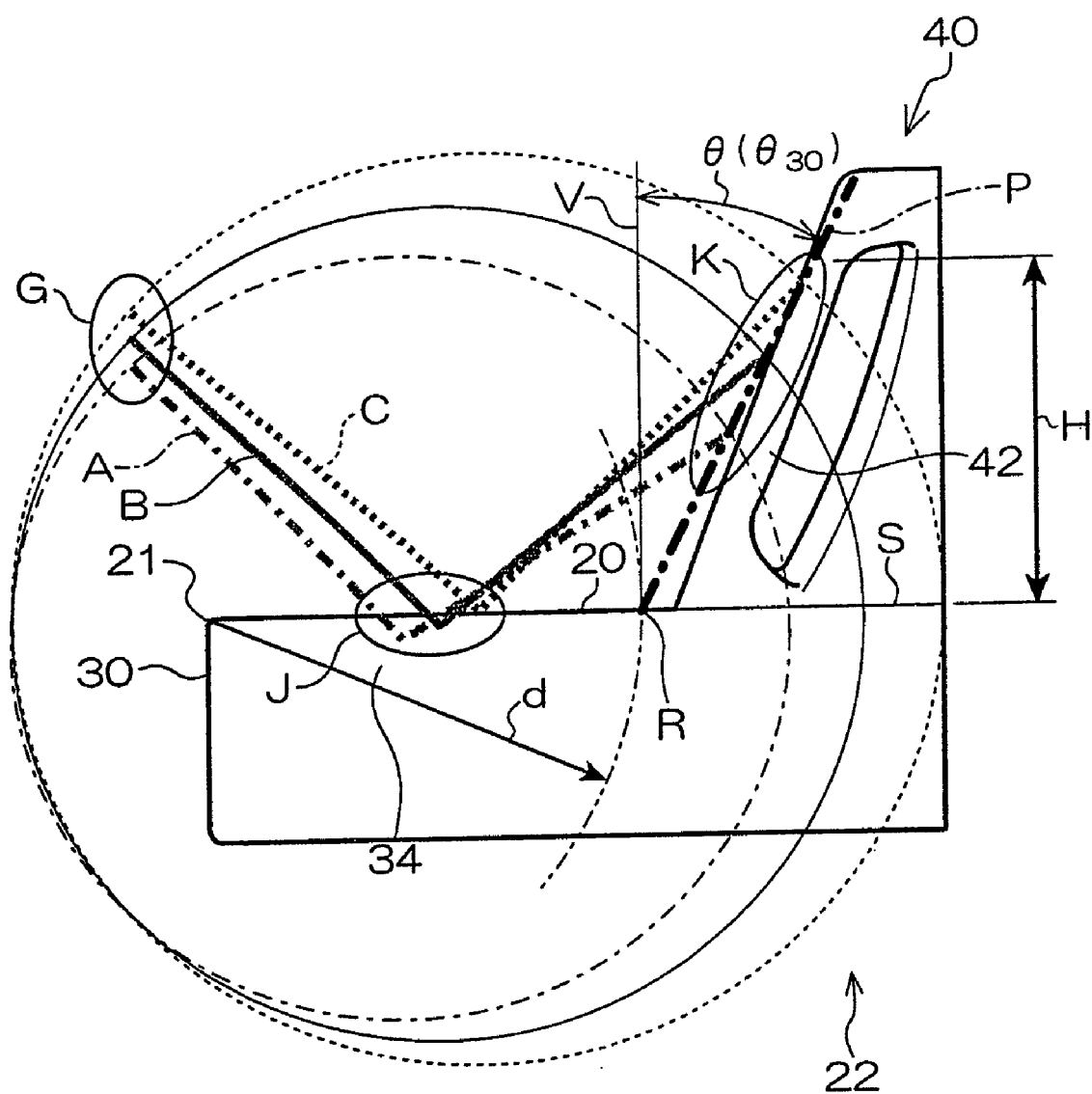
FIG. 5 is a schematic side view describing an examinee being able to grip the handles, regardless of whether the examinee is tall or short or whether the arms of the examinee are long or short, during CC imaging in the X-ray imaging apparatus pertaining to the embodiment of the present invention.

FIG. 5 shows a case where, during CC imaging, the distance d is 300 mm and the front side angle-of-inclination θ of the grip portions 42 is $\theta_{30}$=30°. Further, FIG. 6 shows a case where, during CC imaging, the distance d is 400 mm and the front side angle-of-inclination θ of the grip portions 42 is $\theta_{10}$=10°.

When the distance d is 300 mm and the front side angle-of-inclination θ of the grip portions 42 is $\theta_{30}$ (30°), that is, when the grip portions 42 are disposed along straight line P indicated by the dark and fat one-dotted chain line in FIG. 5, the arms of examinees of whatever height can be positioned comfortably as indicated by broken lines A to C. When the distance d is shorter than 300 mm, the feeling of comfort on the part of the examinee W is not impaired that much, but it is easy for negative effects to arise, such as it becoming difficult for a technician doing positioning to remove his/her hands after holding down the breast of the examinee W because of the arms of the examinee W. Here, as will be understood from broken line C in FIG. 5, the examinee W grips the higher portions of the grip portions 42 the taller the examinee W is. For this reason, when the distance H of the upper ends 42U of the grip portions 42 from the imaging surface 20 (which distance corresponds to the height from the imaging surface 20 because it is during CC imaging) is shorter than 200 mm, it is easy for positioning with respect to an examinee who is tall and the function of the grip portions 42 serving as armrests to be impaired.

Figure 6:
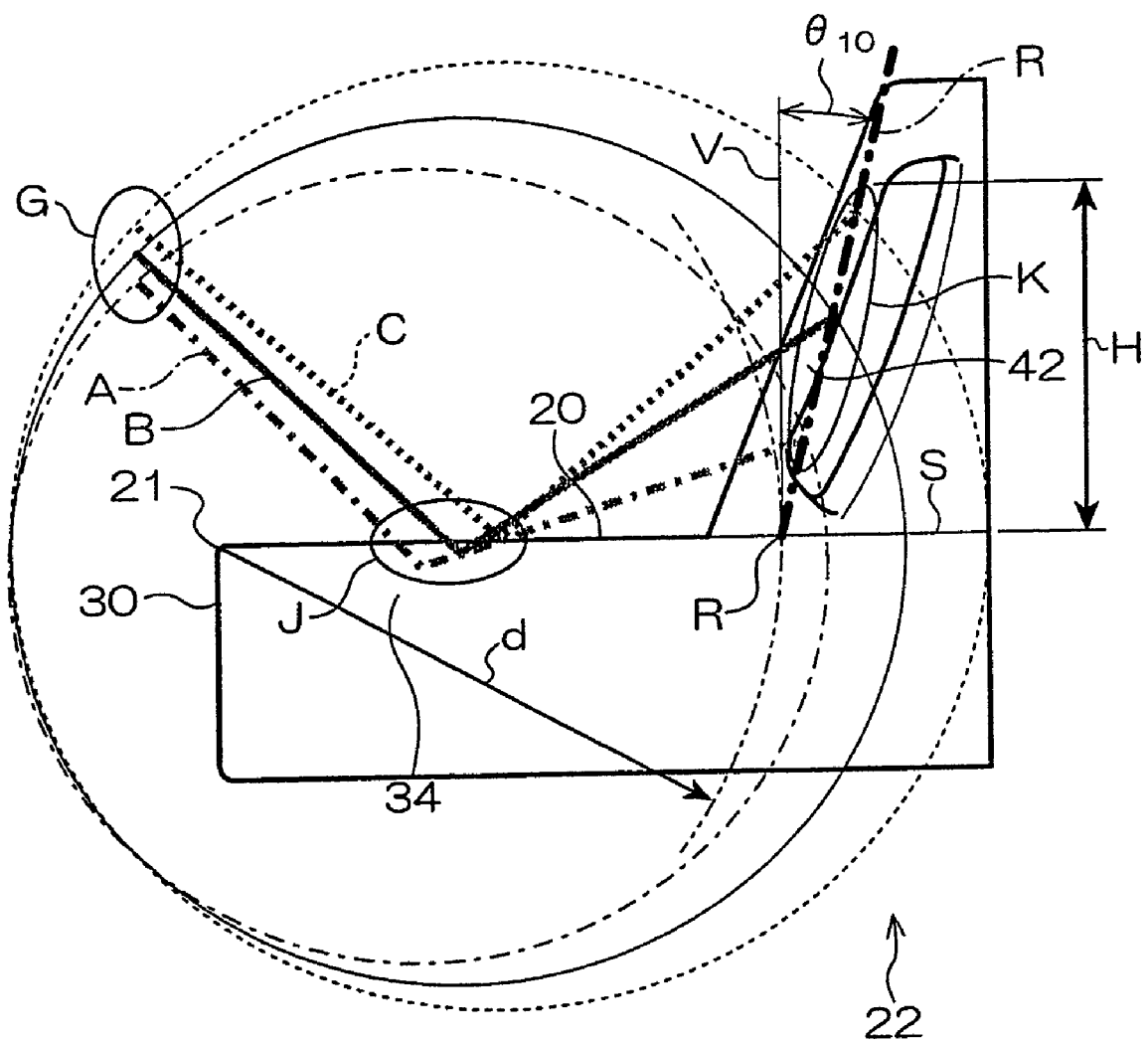
FIG. 6 is a schematic side view describing an examinee being able to grip the handles, regardless of whether the examinee is tall or short or whether the arms of the examinee are long or short, during CC imaging in the X-ray imaging apparatus pertaining to the embodiment of the present invention.

Further, when the distance d is 400 mm and the front side angle-of-inclination θ is $θ_{10}$ (10°), that is, when the grip portions 42 are disposed along straight line R indicated by the dark and fat one-dotted chain line in FIG. 6, the arms of examinees of whatever height can be positioned comfortably as indicated by broken lines A to C. As will be understood from broken line A in FIG. 6, the examinee W grips the lower portions of the grip portions 42 the shorter the examinee W is. Consequently, when the front side angle-of-inclination θ is smaller than 10°, an examinee who is short spreads apart the elbows too much and it becomes difficult for the examinee to grip the grip portions 42 in a natural positioning of the arms, so it is easy for the feeling of comfort of the examinee to be impaired.

Figure 7:
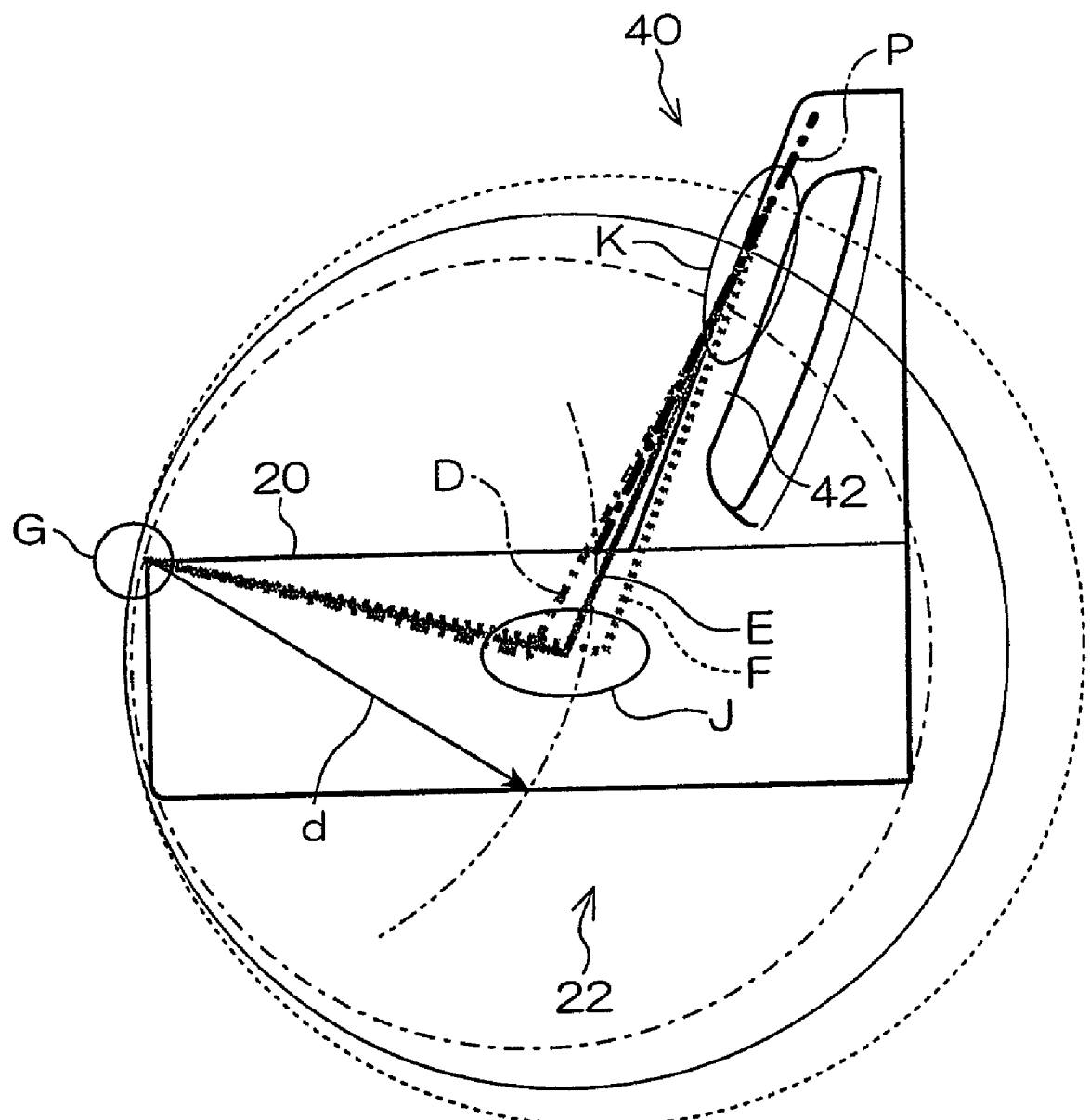
FIG. 7 is a schematic plan view describing an examinee being able to use the handles as armrests, regardless of whether the examinee is tall or short or whether the arms of the examinee are long or short, during MLO imaging in the X-ray imaging apparatus pertaining to the embodiment of the present invention.
Figure 8:
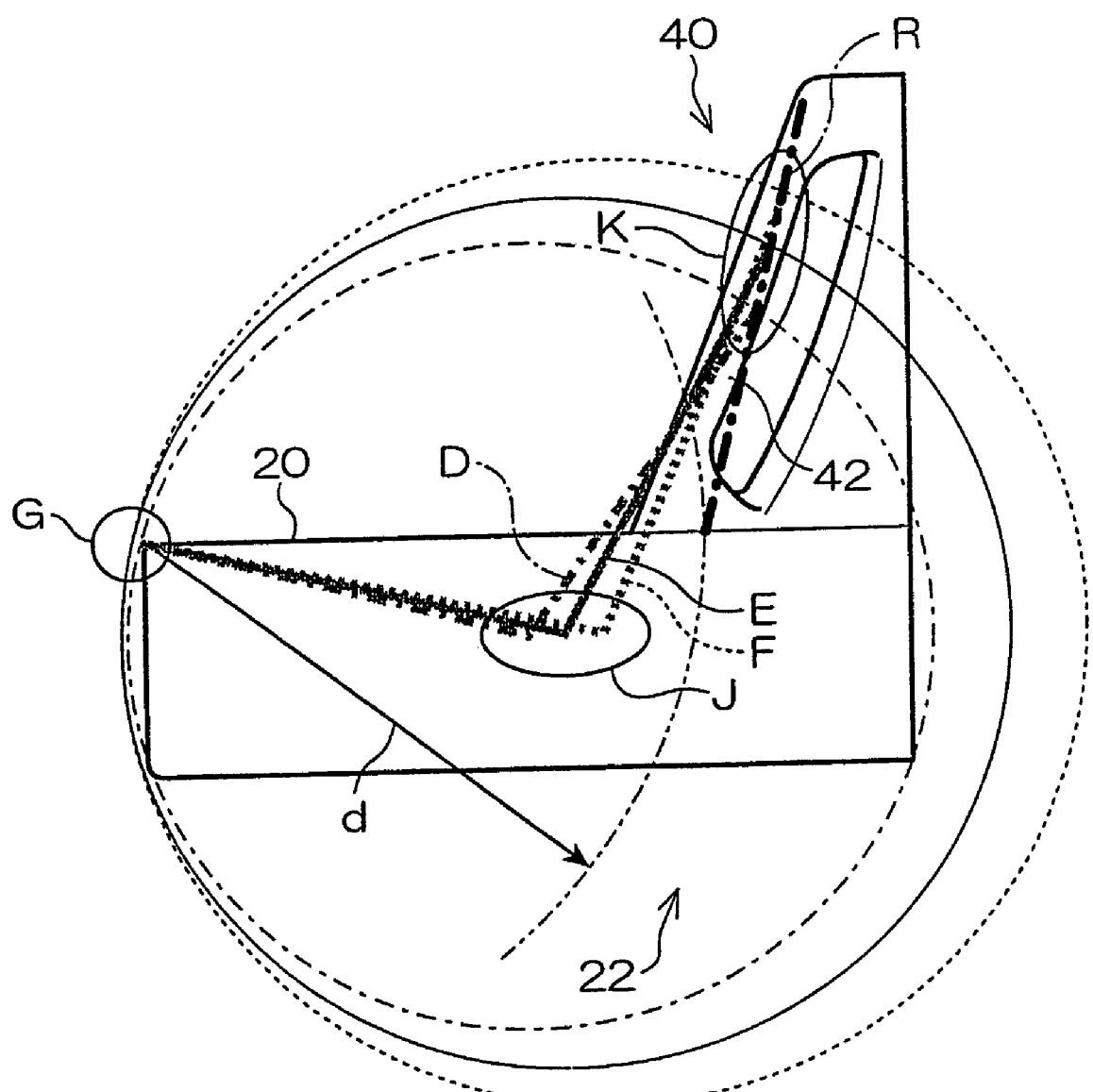
FIG. 8 is a schematic plan view describing an examinee being able to use the handles as armrests, regardless of whether the examinee is tall or short or whether the arms of the examinee are long or short, during MLO imaging in the X-ray imaging apparatus pertaining to the embodiment of the present invention.

FIG. 7 shows a case where, during MLO imaging, the distance d is 300 mm and the front side angle-of-inclination θ of the grip portions 42 is $θ_{30}$=30°. Further, FIG. 8 shows a case where, during MLO imaging, the distance d is 400 mm and the front side angle-of-inclination θ of the grip portions 42 is $θ_{10}$=10°.

When the distance d is 300 mm and the front side angle-of-inclination Θ of the grip portions 42 is $θ_{30}$ (30°), as will be understood from straight lines D to F in FIG. 7, examinees of whatever height can use the grip portions 42 as comfortable armrests. Further, even when the distance d is 400 mm and the front side angle-of-inclination θ is $θ_{10}$ (10°), as will be understood from straight lines D to F in FIG. 8, examinees of whatever height can use the grip portions 42 as comfortable armrests, and a situation where the arms of the examinee directly touch the edge of the imaging table 22 can be avoided.

In order to further raise the effect of examinees being able use the grip portions 42 as armrests during MLO imaging, as shown in FIG. 2, it is preferable for the pair of handles 40 to slant such that they gradually curve toward the inside of the imaging surface 20 as the handles 40 recede from the imaging surface 20. It is preferable for the inside angle-of-inclination δ of the handles 40 (that is, the inside angle-of-inclination of the grip portions 42) to be within the range of 0° to 26° as shown in FIG. 2. Because of this inclination, during CC imaging, the arms of the examinee embrace the imaging table 22 from the shoulders to the hands and, furthermore, during MLO imaging, the arms of the examinee assume a posture inclined a little downward from the shoulders to the hands, so that in both, the examinee can assume a positioning that is more comfortable.

As described above, in the present embodiment, the grip portions 42 slant so as to gradually become closer to the examinee W side as the grip portions 42 approach the imaging surface 20. Additionally, the height position of the upper ends 42U of the grip portions 42 is set to be equal to or greater than 200 mm from the imaging table 22, and the front side angle-of-inclination θ of the grip portions 42 is set within the range of 20±10° (10° to 30°). Further, the distance d from the edge portion 21 of the imaging surface 20 on the examinee W side to the point of intersection R is set to be within the range of 350 mm±50 mm.

Thus, when the examinee W is made to grip the grip portions 42 of the handles 40, the posture of the examinee can be made more natural, and the examinee W can be made positioned comfortably and imaged. Further, regardless of whether the examinee W is tall or short or whether the arms of the examinee W are long or short, it can be sufficiently ensured that the examinee W can be positioned in a natural posture during CC imaging and that the examinee W can use the handles 40 as armrests during MLO imaging. These facts offer large effects to an examinee that is physically disabled and has difficulty maintaining an upright posture.

Further, the handles 40 are formed integrally with the imaging table 22. Consequently, the comfort of the armrests can be promoted because joints disappear. Further, when the imaging table 22 is rotated in order to perform MLO imaging, the handles 40 rotate together with the imaging table 22.

Further, the handles 40 are configured by soft members. Thus, the feeling of gripping the handles 40 is comfortable for the examinee W.

Figure 9:
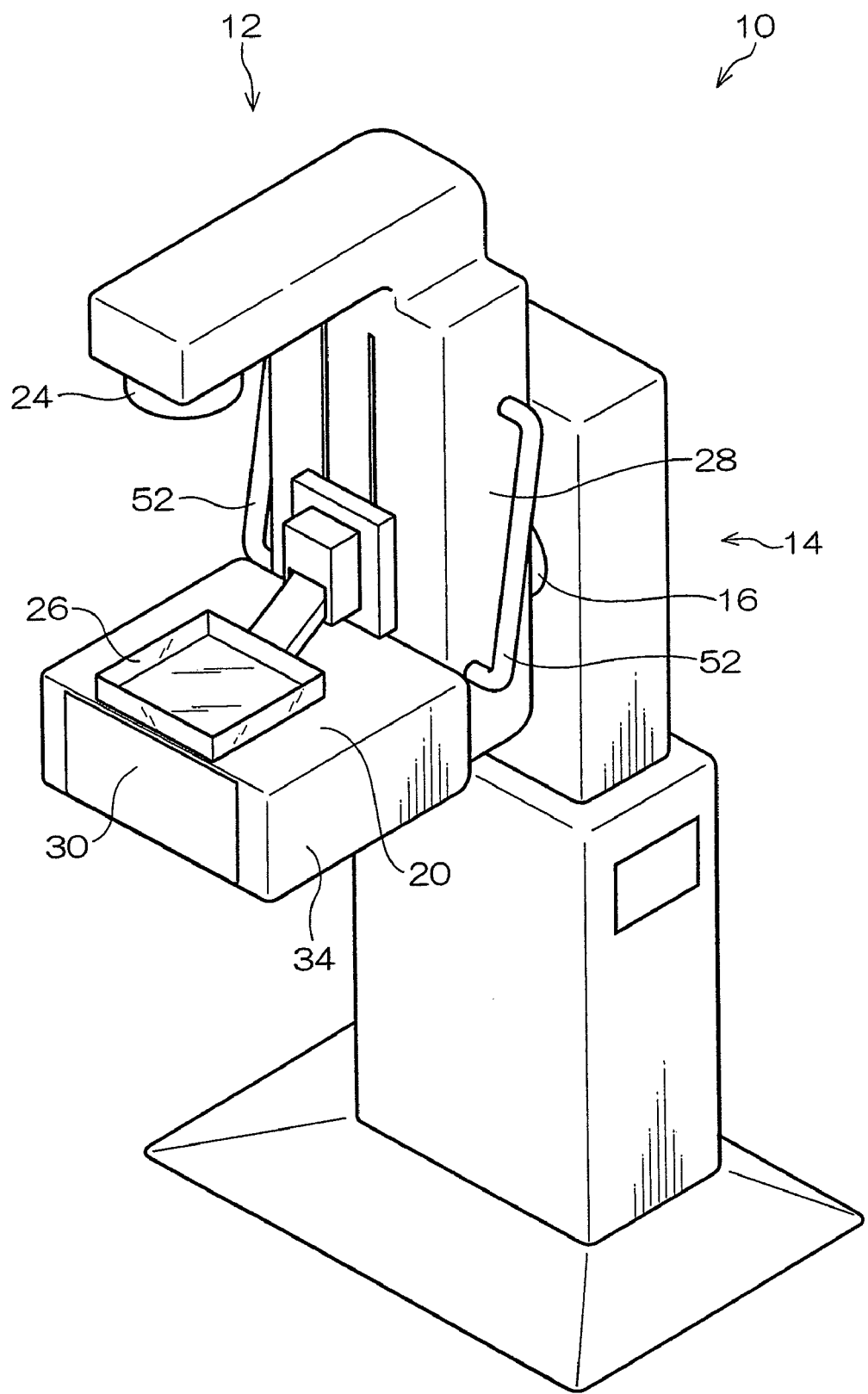
FIG. 9 is a perspective view of a modification of the X-ray imaging apparatus pertaining to the embodiment of the present invention.

It will be noted that, in the present embodiment, the X-ray imaging apparatus 10 where the handles 42 are formed integrally with the imaging table 22 has been described, but as shown in FIG. 9, rather than forming the handles on the imaging table, handles 52 may also be formed on the holding portion 28. Similar to the handles 42, the handles 52 slant so as to gradually become closer to the examinee W side as the handles 52 approach the imaging surface 20. Thus, similar to when the handles 42 are disposed, when the examinee W is made to grip the handles 52, the posture of the examinee W can be made more natural, and the examinee W can be positioned comfortably and imaged. Further, the examinee W can be positioned in a natural posture during CC imaging regardless of whether the examinee W is tall or short or whether the arms of the examinee W are long or short.

A mode of implementing the present invention has been described above by way of an embodiment, but the above-described embodiment is one example and can be variously changed and implemented within a range that does not depart from the gist of the invention. Further, it goes without saying that the scope of rights of the invention is not limited to the above-described embodiment. For example, the X-ray imaging apparatus that is used in the exemplary embodiment of the present invention may be a screen-film related apparatus using radiosensitizing paper and silver film, a computed radiography apparatus using photostimulable phosphor or a digital radiography apparatus using a solid state sensor.

What is claimed is:

1. An X-ray imaging apparatus that images the breasts of an examinee, the examinee's upper body having an upright posture, the X-ray imaging apparatus comprising:
   an imaging table that includes an imaging surface with which at least one breast of the examinee is brought into contact;
   apparatus grasping portions that are disposed higher than the imaging surface during craniocaudal imaging, the grasping portions being configured to be graspable by the hands of the examinee, and slant so as to gradually become closer to the examinee as the grasping portions approach the imaging surface; and
   the apparatus grasping portions curve toward the inside of the imaging surface.

2. The X-ray imaging apparatus of claim 1, wherein the apparatus grasping portions comprise handles that include grip portions having a bar shape that are equal to or greater than a predetermined length.

3. The X-ray imaging apparatus of claim 2, wherein the grip portions slant in accordance with the average height of the examinee.

4. The X-ray imaging apparatus of claim 2, wherein the grip portions slant in accordance with the average arm length of the examinee.

5. The X-ray imaging apparatus of claim 2, wherein the grip portions slant by an angle within the range of 20°±10° in a front direction of the examinee during craniocaudal imaging with respect to a normal line direction of the imaging surface.

6. The X-ray imaging apparatus of claim 5, wherein a distance from a point of intersection between an extension plane of the imaging surface and a center of the grip portions to an edge portion of the imaging surface on the examinee side is within the range of 350 mm±50 mm.

7. The X-ray imaging apparatus of claim 6, wherein a height position of upper ends of the grip portions during craniocaudal imaging is set to be equal to or greater than 200 mm from the imaging surface.

8. The X-ray imaging apparatus of claim 2, wherein the handles are formed integrally with the imaging surface.

9. The X-ray imaging apparatus of claim 2, wherein the handles include soft members.

10. The X-ray imaging apparatus of claim 2, wherein the handles slant so as to gradually curve toward the inside of the imaging surface as the handles recede from the imaging surface.

11. The X-ray imaging apparatus of claim 1, wherein the apparatus grasping portions curve toward a plane that is orthogonal to the imaging surface and extends toward an examinee side, and an angle of the apparatus grasping portions with respect to the plane is equal to or less than 20°.

* * * * *